United States Patent
Greenhaw et al.

(10) Patent No.: US 6,938,621 B1
(45) Date of Patent: Sep. 6, 2005

(54) DISPOSABLE PLUG FOR WARMING THE INNER EAR

(76) Inventors: Sareva L. Greenhaw, 13547 E. 38th St., Tulsa, OK (US) 74134; Lamberto Dionigi, Via della Repubblica 39, 53035 Monteriggioni (loc. S. Martino), SI (IT)

( * ) Notice: Subject to any disclaimer, the term of this patent is extended or adjusted under 35 U.S.C. 154(b) by 0 days.

(21) Appl. No.: 10/911,273

(22) Filed: Aug. 4, 2004

(51) Int. Cl.[7] ............................................. A61F 11/00
(52) U.S. Cl. ...................... 128/864; 128/865; 181/129; 181/130
(58) Field of Search ................. 128/864, 865, 128/866, 867, 868; 181/129, 130, 131, 132, 181/133, 134, 135; D24/106

(56) References Cited

U.S. PATENT DOCUMENTS

| | | | |
|---|---|---|---|
| 2,804,072 A | * | 8/1957 | Genzer ..................... 128/864 |
| 3,047,089 A | * | 7/1962 | Zwislocki ................. 181/135 |
| 3,796,855 A | | 3/1974 | Brown |
| 3,872,559 A | * | 3/1975 | Leight ...................... 128/867 |
| 4,094,315 A | * | 6/1978 | Leight ...................... 128/864 |
| D253,723 S | * | 12/1979 | Leight ..................... D24/106 |
| 4,253,452 A | * | 3/1981 | Powers et al. ............ 128/864 |
| 4,408,605 A | | 10/1983 | Doerr et al. |
| 4,434,794 A | * | 3/1984 | Leight ...................... 128/867 |
| 4,522,190 A | | 6/1985 | Kuhn et al. |
| 4,564,009 A | * | 1/1986 | Brinkhoff .................. 128/864 |
| 4,806,186 A | * | 2/1989 | Sirkin et al. .............. 128/864 |
| 5,009,228 A | | 4/1991 | Clark |
| 5,080,110 A | | 1/1992 | Weldon et al. |
| 5,197,974 A | | 3/1993 | Scarpelli et al. |
| 5,456,703 A | | 10/1995 | Beeuwkes, III |
| 5,483,027 A | | 1/1996 | Krause |
| D371,840 S | | 7/1996 | Leight |
| 5,809,573 A | | 9/1998 | Bary |
| 5,954,682 A | | 9/1999 | Petrus |
| 6,016,574 A | | 1/2000 | Chen |
| 6,056,082 A | * | 5/2000 | Lindgren et al. ........... 181/130 |
| 6,093,202 A | | 7/2000 | Dyken et al. |
| 6,341,602 B1 | | 1/2002 | Fulcher |
| 6,345,737 B1 | | 2/2002 | Martin et al. |
| 6,830,124 B2 | * | 12/2004 | Chiang ..................... 181/135 |
| 2002/0035340 A1 | | 3/2002 | Fraden et al. |

* cited by examiner

*Primary Examiner*—Fadi H. Dahbour
(74) *Attorney, Agent, or Firm*—Frank J. Catalano

(57) ABSTRACT

A disposable plug has a mask with an orifice aligned at the entry into the ear canal when the plug is inserted into the ear. A sealed envelope has a leading elastic tip that extends forward of the orifice into the ear canal and a trailing reservoir that extends rearward of the orifice. A super-cooled liquid salt substantially fills the envelope. The envelope is sized to contain a sufficient quantity of the liquid salt to deliver heat to the inner ear at a predetermined temperature for a predetermined time period. A convex disk in the reservoir can be manually popped to concave after the tip of the envelope has been inserted into the ear canal to shrink the reservoir and expand the tip into deeper extension into and compliance with the ear canal and to activate solidification of the liquid salt to generate heat into the ear canal.

20 Claims, 3 Drawing Sheets

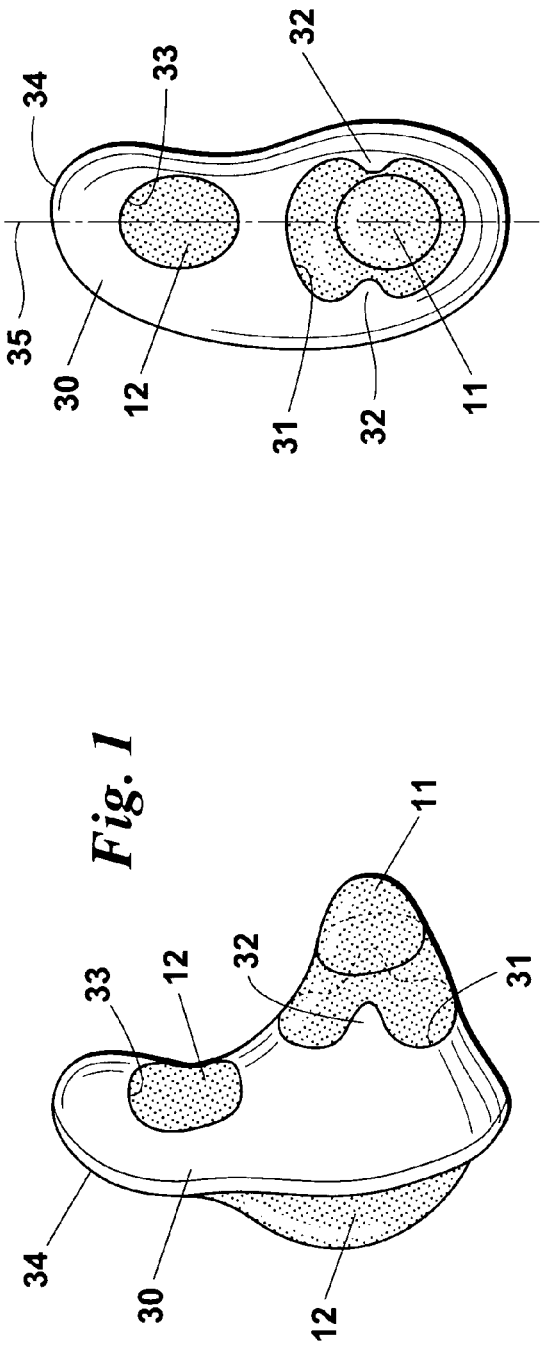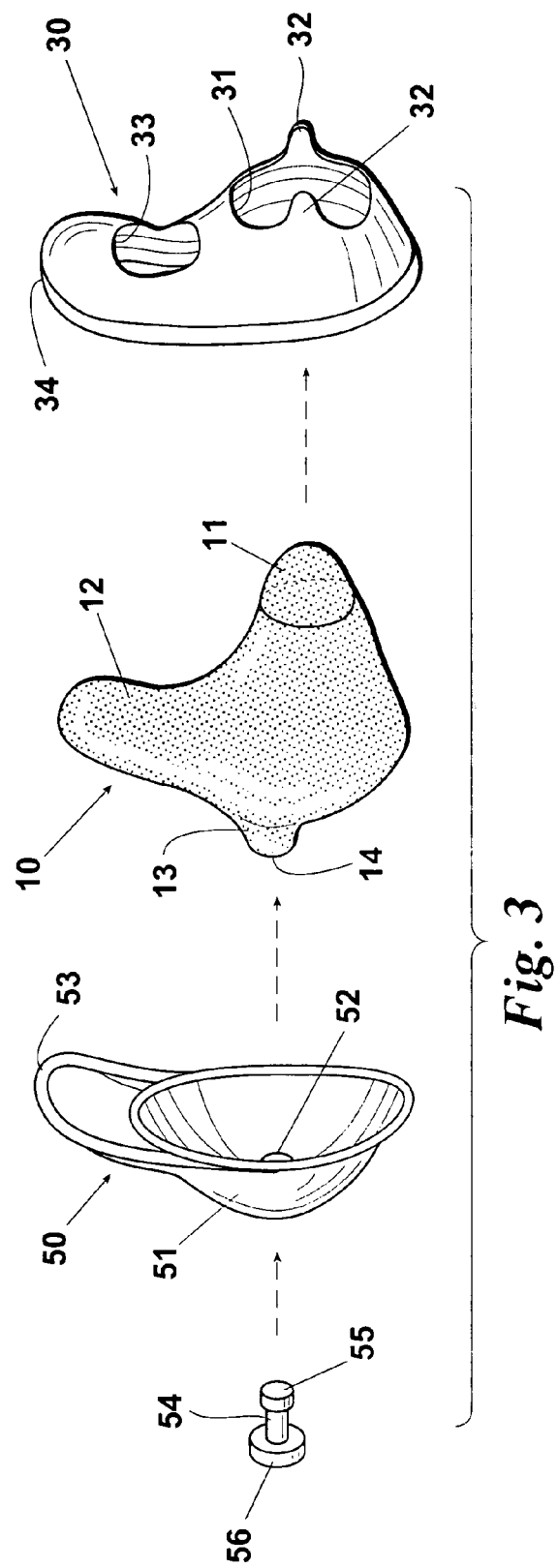

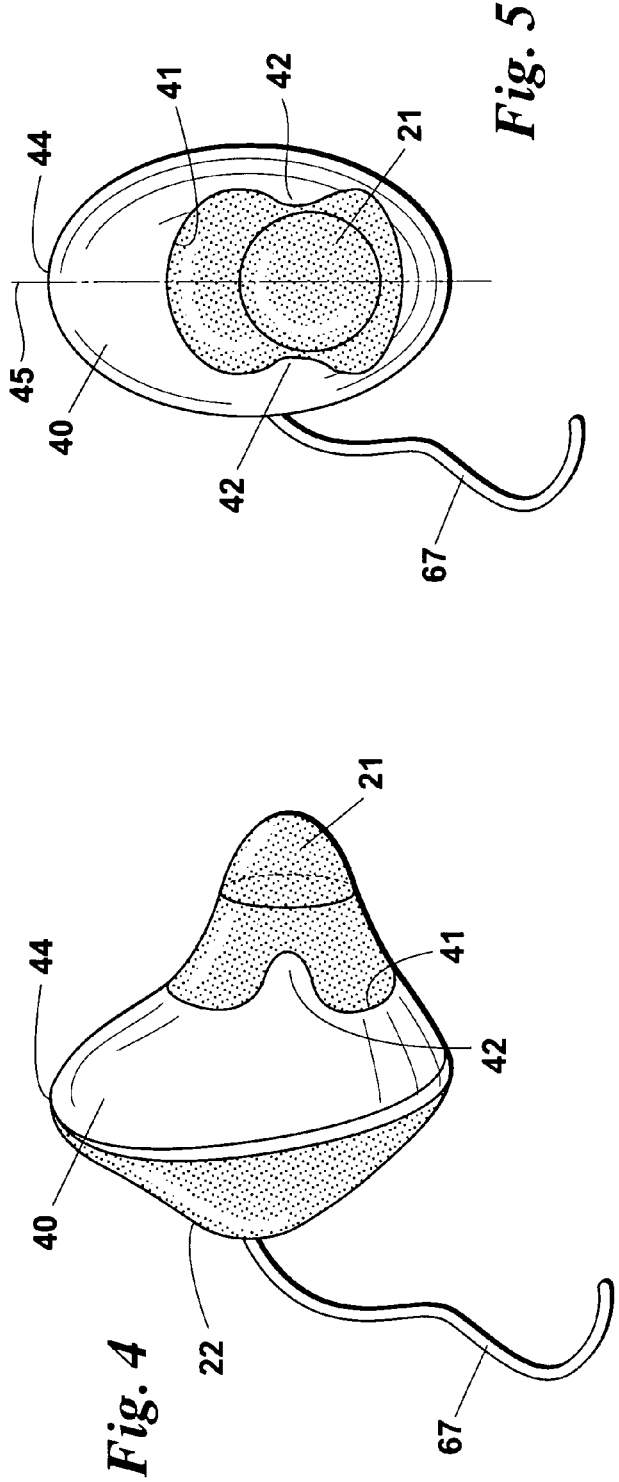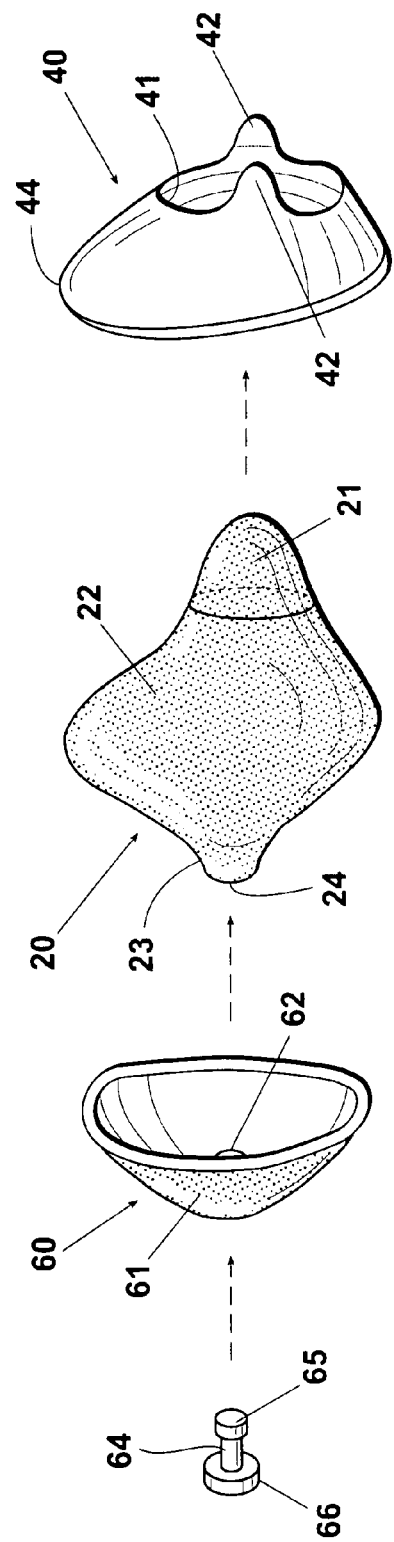

DISPOSABLE PLUG FOR WARMING THE INNER EAR

BACKGROUND OF THE INVENTION

This invention relates generally to devices for therapeutic treatment of the human ear and more particularly concerns a disposable plug for warming the inner ear.

Warming the ear is an accepted method of relieving inner ear pain. Inner ear relief is commonly accomplished, though to a limited extent, by warming the outer ear to achieve a resultant heat transfer to the inner ear. Known outer ear warming devices generally have an insulated housing that covers the outer ear. A hollow chamber within the housing stores a heat source, typically a heated liquid such as hot water or a phase-change salt or oil such as a carboxymethylcellulose mixture. In some of these devices, the heat source is introduced into its chamber for each use. For example, boiling water is poured into the chamber and, after use, the cooled water is drained from the chamber. In others, a permanent heat source is provided in the chamber and the device is placed in a microwave oven or in boiling water to heat the source. The initial temperature of the heat source must be relatively high in order to compensate for the losses incurred during transfer of heat to the inner ear. Even if the source does sufficiently meet the initial temperature requirement so as to be capable of delivering high enough temperatures to the inner ear, the temperature in the chamber drops relatively quickly so that useful warmth is applied to the inner ear for only a very brief time interval. To reduce these heat transfer losses, some devices have multiple chambers with a different heat source liquid in each chamber, the different liquids providing different thermal characteristics so as to afford some control to the temperature level and duration of the heat transfer process. Other devices include permanent heat generating sources such as electrically powered heating coils to control and maintain temperature levels in the device.

All of these devices suffer from one or more common deficiencies. They are not disposable and their heat source must be replaced or reheated each time they are used. They are structurally complex and, therefore, unwieldy for the care-giver and uncomfortable for the patient. They have many rigid components that inhibit adaptability to the unique anatomical structure of individual patients. Their time and temperature controls are so complex as to appreciably increase both their cost and their likelihood of failure. They are generally inefficient, inasmuch as they apply heat directly to the outer ear and only indirectly to the intended target, the inner ear. They are to a great extent impractical, in that their structural design is dedicated to their conformance to the outer ear while their objective is to transfer warmth to the inner ear.

It is, therefore, an object of this invention to provide an ear warming plug which is disposable. Another object of this invention is to provide an ear warming plug which is structurally simple. A further object of this invention is to provide an ear warming plug which is easy for a care-giver to handle. Yet another object of this invention is to provide an ear warming plug which is comfortable for the patient. It is also an object of the invention to provide an ear warming plug which adapts to the unique anatomical structure of the patient. Still another object of this invention is to provide an ear warming plug which is inexpensive. An additional object of this invention is to provide an ear warming plug which applies heat directly to the inner ear. Another object of this invention is to provide an ear warming plug which is designed to conform to the contours of the inner ear.

SUMMARY OF THE INVENTION

In accordance with the invention, a disposable plug is provided for generating heat to warm an ear canal. A mask has a leading surface contoured for insertion into the outer ear for abutment against a wall of the outer ear surrounding the entrance to the ear canal. An orifice through the wall of the mask aligns with and at the entry into the ear canal when the plug is inserted into the outer ear and abuts the wall at the entrance. A sealed envelope has a leading tip that extends forward of the orifice and a trailing reservoir that extends rearward of the orifice and the trailing surface of the mask. The leading tip of the envelope is elastic and contoured to extend into the ear canal when the mask abuts the wall at the entrance to the ear canal. The trailing reservoir has a forward wall, a main body and a rear wall. The forward wall of the reservoir is contoured to comply against the trailing surface of the mask. A super-cooled liquid salt substantially fills the envelope. The envelope is sized to contain a sufficient quantity of the liquid salt to deliver heat to the inner ear at a predetermined temperature for a predetermined time period. A disk which is convex in relation to the mask is disposed in the reservoir and immersed in the liquid salt. The rear wall of the reservoir is connected to the disk. The periphery of the body of the reservoir taken along a generally vertical plane is clamped between the periphery of the mask and the periphery of the disk. As a result of this peripheral clamping, when the mask abuts the wall of the outer ear and the disk is pressed toward the mask, the disk will pop from convex to concave. Popping the disk from convex to concave decreases the volume of the reservoir, expands the tip into deeper extension into and compliance with the ear canal and activates solidification of the liquid salt to generate heat into the ear canal.

The envelope is preferably made of polyurethane. The envelope walls are either of constant thickness or the walls of the envelope tip are thinner than the walls of the envelope reservoir so as to facilitate extension of the tip internal conformance of the tip with the contour of the inner ear while maximizing the strength of the reservoir. The tip of the envelope and the mask may be contoured to suit either a left or right ear or may be symmetrical in relation to a vertical plane so that the same plug may be used in either the left or right ear. The envelope is preferably hermetically sealed and may have thermochromatic pigmentation which will provide an alert if inadvertent or premature activation of the plug has occurred or will indicate the thermal state of the plug during its proper use. The mask is sufficiently rigid to provide a defined shape to the envelope reservoir and to facilitate the popping action of the disk within the reservoir. Preferably, the mask has a second orifice, most preferably above the ear canal orifice, to maximize the transfer of heat toward the inner ear. The convex disk is preferably metallic and has an opening at approximately its apex. A cap secures a portion of the rear wall of the reservoir in the opening so to fix the rear wall of the reservoir to the disk. The preferred liquid salt is a water solution of sodium acetate.

BRIEF DESCRIPTION OF THE DRAWINGS

Other objects and advantages of the invention will become apparent upon reading the following detailed description and upon reference to the drawings in which:

FIG. 1 is a side perspective view of an asymmetric embodiment of the disposable plug;

FIG. 2 is a front elevation view of the plug of FIG. 1;

FIG. 3 is a side perspective assembly view of the plug of FIG. 1;

FIG. 4 is a side perspective view of a symmetric embodiment of the disposable plug;

FIG. 5 is a front elevation view of the plug of FIG. 4;

FIG. 6 is a side perspective assembly view of the plug of FIG. 4;

Figure 7:
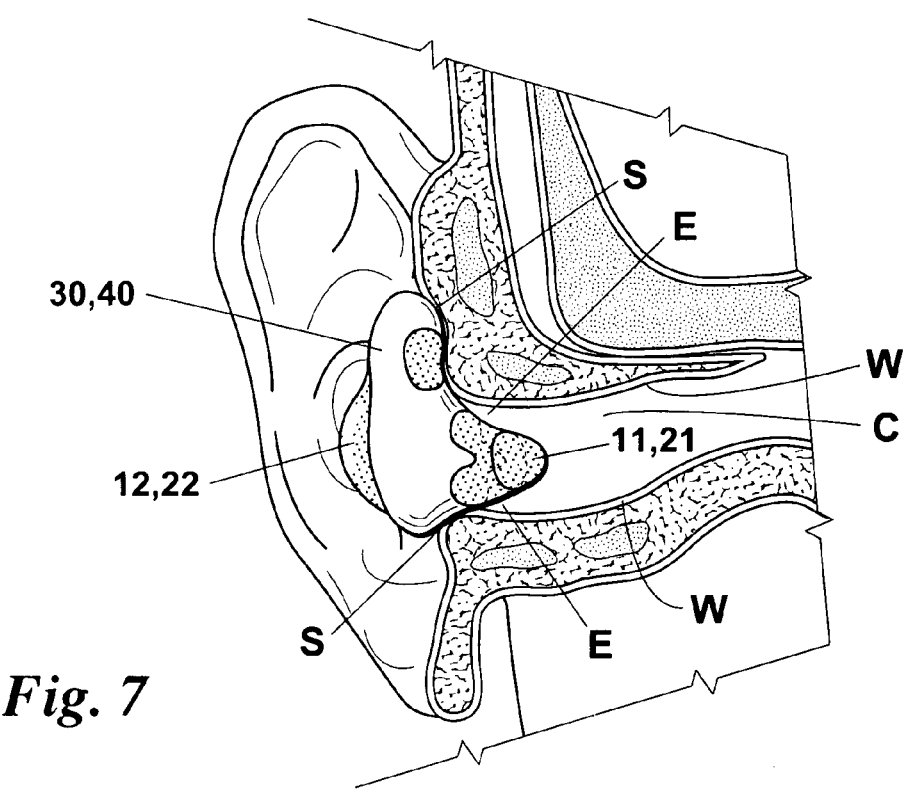
FIG. 7 is a side elevation view of a plug after insertion into the ear and prior to activation.

While the invention will be described in connection with preferred embodiments thereof, it will be understood that it is not intended to limit the invention to those embodiments or to the details of the construction or arrangement of parts illustrated in the accompanying drawings.

DETAILED DESCRIPTION

Looking at the FIGS. 1–3, an asymmetrical embodiment of a disposable plug for generating heat to warm an ear canal is illustrated. As best seen in FIG. 3, the principle structural components of the asymmetrical plug are an envelope 10, a mask 30 and a trigger 50.

The Envelope

The primary functions of the envelope 10 or 20 are to contain the phase-change heat-generating chemicals of the plug and to penetrate into and conform to the ear canal C in the initial stages of activation. The envelope 10 or 20 has two major portions, a leading tip 11 or 21 and a trailing reservoir 12 or 22. In the pre-activated state of the plug the entire envelope 10 or 20, including the tip 11 or 21 and the reservoir 12 or 22, is substantially filled by the phase-change chemicals in their liquid state. The envelope 10 or 20 can be formed from a variety of materials. Rubber compounds such as bromobutyl rubber have sufficient strength and elasticity. Latex blends are generally more resilient than rubber. Polyurethane is compatible with more chemicals than latex, causes generally less allergic reaction of the skin than latex and is a better heat conductor. Whatever the material chosen, its thickness should be great enough to afford the strength necessary to contain the phase-change chemicals without rupture during storage, activation and operation of the plug, yet elastic enough to permit expansion of the top of the plug during operation, as will be hereinafter explained. Considering the requirements of the envelope 10 or 20 and the advantages and disadvantages of the various materials from which it could be formed, the presently preferred material is polyurethane, approximately 0.04 to 0.07 millimeters thick.

The phase-change chemical substantially filling the envelope is preferably a super cooled liquid salt which is compatible with the selected envelope material. If the envelope 10 or 20 is made of polyurethane, a water solution of sodium acetate, $3H_2O*CH_3\ COONa$, is suitable. A thermo-chromatic pigmentation may be included in the envelope material so as to affect a change in the color of the envelope 10 when the solidification process is activated. A change in envelope color would, therefor, serve as a warning of premature or inadvertent activation of the plug or as confirmation of appropriate heat transfer during the intended operation of the plug.

Figure 8:
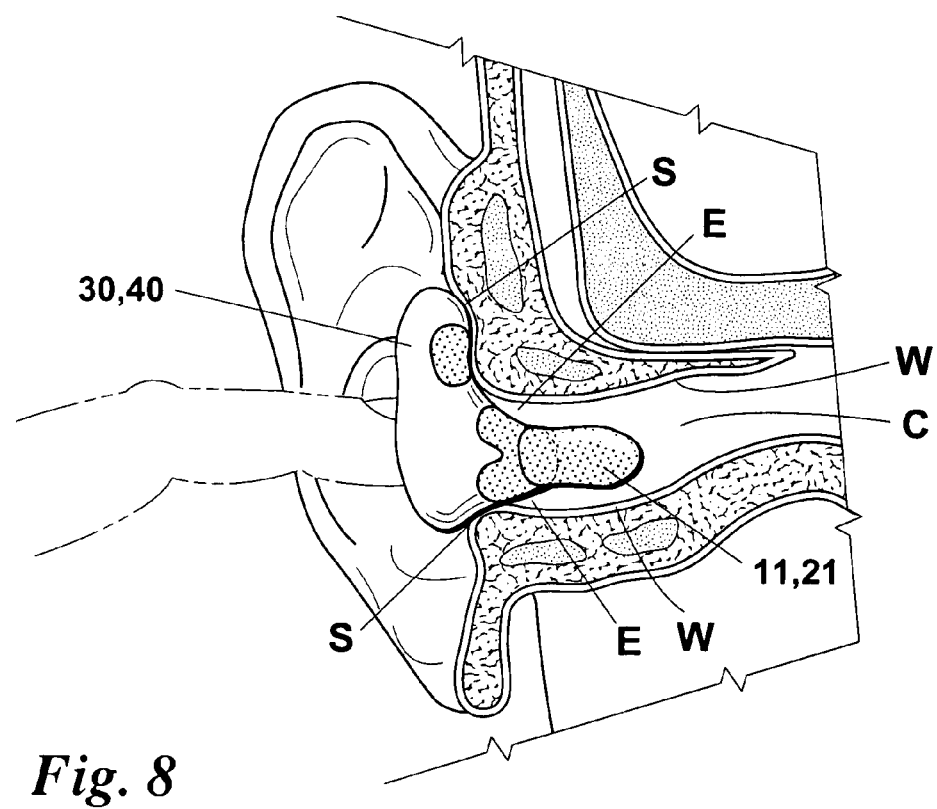
FIG. 8 is a side elevation view of a plug after insertion into the ear- and during activation.

As best seen in FIG. 7, the leading tip 11 or 21 of the envelope 10 or 20 is contoured for comfortable insertion into the ear canal C while the phase-change chemicals are in their liquid pre-activated state. While the thickness of the overall envelope 10 or 20 is selected in the accordance with the general criteria outlined above, the tip 11 or 12 must further be of suitable elasticity to facilitate extension of the tip 11 or 12 more deeply into the canal C and expansion of the tip 11 or 12 into greater compliance with the walls W of the ear canal C as the volume of the tip 11 or 12 is increased during the early stages of the activation process, as is seen in FIG. 8. The reservoir 12 or 22 of the envelope 10 or 20 is contoured generally for elastic compliance with the trailing surface of the mask 30 or 40, as will hereinafter be explained. The reservoir 12 or 22 is sized so that the total volume of the envelope 10 or 20 in its soft pre-activated state will, when substantially filled, contain a sufficient amount of phase-change chemicals to maintain the expanded portion of the leading tip 11 or 12 of the envelope 10 or 20 at a pre-selected temperature for a pre-selected time interval. During operation of the plug it is desirable to maintain a temperature of approximately 104° F. for at least approximately 13 to 15 minutes. Its thickness is such as to afford the necessary strength to maintain its integrity throughout the lifetime of the plug and especially during the exertion of the forces necessary for the activation and operation of the plug, as hereafter explained. Several other factors also contribute to the overall shape of the reservoir 12 or 22. The forward portion of the reservoir 12 or 22 is contoured to readily comply with the trailing surface of the mask 30 or 40. Since, in addition to the phase-change chemicals, the envelope 12 or 22 will also contain the activation trigger 50 or 60, a portion of the reservoir 12 or 22, in the embodiment shown the rear wall of the reservoir 12 or 22, may be contoured to adapt to the activation trigger 50 or 60. Also, as best seen in FIGS. 3 and 6, the reservoir 12 or 22 may include a throat 13 or 23 with an aperture 14 or 24 through which the trigger 50 or 60 and liquid salt can be inserted and injected into the envelope 10 or 20. The aperture 14 or 24 may be approximately 2 millimeters in diameter, expandable to receive the structure of the activating trigger 50 or 60 and, after insertion of the trigger 50 or 60, to return to its normal diameter to be filled with the change-phase chemicals. After the trigger 50 or 60 and chemicals have been inserted and injected into the reservoir 12 or 22, the aperture 14 or 24 can be hermetically sealed by the application of heat, glue, or such other method as may be required by the material of the envelope 10 or 20.

A relatively constant thickness can be selected for the entire envelope 10 or 20 which is more specially suited to either the expanding and conforming functions of the tip 11 or 21 or to the overall strength requirements of the envelope 10 or 20. For example, a polyurethane envelope 10 or 20 in the order of approximately 0.07 millimeters thickness would provide greater strength, while a polyurethane envelope 10 or 20 of thickness in the order of approximately 0.05 millimeters would provide greater penetration and expansion of the tip 11 or 12 in the ear canal C. Alternatively, the envelope 10 or 20 can have a reservoir 12 or 22 of a first relatively constant thickness so as to maximize the strength characteristics of a substantial portion of the envelope 10 or 20 and a tip 11 or 12 of a second, thinner, relatively constant thickness so as to facilitate maximum expansion of the tip 11 or 12. Both advantages could be obtained, for example, if the reservoir 12 or 22 has a thickness of approximately 0.07 millimeters while the tip 11 or 21 is somewhat thinner with a thickness of approximately 0.05 millimeters.

In the operation of the plug, as is hereafter explained, the thinner wall of the envelope 10 or 20 will allow for greater penetration of the tip 11 or 21 into the ear canal C and for greater compliance or adherence of the tip 11 or 21 to the contours of the walls W of the ear canal C which generally have an irregular shape. In the early stages of operation after activation of the plug, the tip 11 or 21 containing the liquid salt is still soft and able to conform to the irregularities of the ear canal C. The chemicals in the tip 11 or 21 will crystallize and solidify within approximately the first 30 seconds after activation. By the end of the solidification period, the tip 11 or 21 is permanently expanded into its conformal condition within the ear canal C. The warmth generated by the plug will thereafter be directly applied to the walls W of the ear canal C for the remainder of the approximately 13–15 minute operating period.

The Mask

The mask 30 or 40 serves multiple functions plug as a generally stabilizing structure for the ear plug. While it is not absolutely rigid, it is sufficiently rigid to provide structural definition for the elastic envelope 10 or 20. It serves as a barrier with an orifice 31 or 41 from which the elastic tip 11 or 21 forwardly extends for insertion into the ear canal C and the trailing reservoir 12 or 22 rearwardly extends. It provides a structurally defined surface suitable for abutment with the surface S of the outer ear surrounding the entry E to the ear canal C, as is best seen in FIGS. 7 and 8. It focuses the transfer of heat through the orifice 31 or 41 toward the ear canal C. The mask 30 or 40 also affords a co-operable structure for securing the trigger 50 or 60 within the envelope 10 or 20 and for facilitating operation of the trigger 50 or 60 to activate the plug.

Preferably, the mask 30 or 40 is contoured to provide grooves 32 or 42 extending rearwardly from the perimeter of the orifice 31 or 41. The grooves 32 or 42 relieve the accumulation of air in the ear canal C as the tip 11 or 21 of the envelope 10 or 20 is complied to the ear canal C during the early stages following activation of the plug. The perimeter of the orifice 31 or 41 can be extended inwardly toward the ear canal C to maximize the depth of penetration of the air grooves 32 or 42 toward the ear canal C. However, the mask 30 or 40 does not penetrate into ear canal C. Relief is provided because the tip 11 or 21 of the envelope 10 or 20 is contoured by the grooves 32 or 42 so that proximate the ends of the grooves 32 or 42, the tip 11 or 21 cannot fully contour to the ear. The mask 30 or 40 may also be provided with an upper orifice 33 or 43. Some of the heat generated during the chemical phase change will be lost rearwardly of the mask 30 or 40. The upper orifice 33 or 43 reduces the heat loss by facilitating application of that heat to the outer ear. The mask 30 or 40 also has a perimeter 34 or 44 which, as noted above, is co-operable with the trigger 50 or 60 which is hereinafter described. The mask 30 or 40 is preferably formed of thin plastic such as polyethylene or polypropylene.

The Trigger

The trigger 50 or 60 facilitates activation of the heat generating process of the plug and directs extension and expansion of the elastic tip 11 or 21 of the envelope 10 or 20 in the ear canal C, as best seen in FIG. 8. The structure of the activation trigger 50 or 60 may be modified to conform to the size requirements of the reservoir 12 or 22.

The trigger 50 or 60 includes a disk 51 or 61 which, as best seen in FIGS. 3 and 6, is convex relative to the mask 30 or 40 prior to activation of the plug. An opening 51 or 62, preferably at the apex of the convex disk 51 or 61, aligns with the aperture 14 or 24 of the envelope 10 or 20 when the disk 51 or 61 is inserted through the aperture 14 or 24 and the rear surface of the disk 51 or 61 abuts the inner surface of the back portion of the reservoir 12 or 22. Thus the forward wall of the reservoir 12 or 22 complies to the rear surface of the mask 30 or 40 and the rear wall of the reservoir 12 or 22 complies to the surface of the convex disk 51 or 61. If the perimeter of the reservoir 12 or 22 were coordinated only to the size of the disk 51 or 61, the reservoir 12 or 22 might not afford sufficient volume in the envelope 12 or 22 for the necessary quantity of phase change chemicals. In this case, additional support structure 53 can be appended to the perimeter of the disk 51 to increase the total perimeter of the trigger 50 and, therefore, accommodate a larger reservoir 12. The added structure 63 has been illustrated in relation to the asymmetrical embodiment of the plug, while the symmetrical embodiment has been illustrated without added structure. However, either embodiment could be made with or without added structure, as required. The trigger 50 or 60 and particularly the disk 51 or 61 are preferably formed of stainless steel. A cap 54 or 64, preferably formed of plastic, is insertable through the aperture 14 or 24 in the throat 13 or 23 of the envelope 12 or 22. The cap 54 or 64 has a resiliently compressible tip 55 or 65 and a wide base 56 or 66. The tip 55 or 65 will snap into and plug the opening 52 or 62 in the disk 50 or 60 and its wide base 56 or 66 will secure the throat 13 or 23 of the envelope 10 or 20 to the back of the disk 51 or 61 so that the envelope 10 or 20 will follow the contour of the disk 51 or 61 as it pops from convex to concave.

Assembly

The mask 30 or 40 has been shaped so that its leading surface conforms to approximately the surface S of the outer ear surrounding the entry E to the ear canal C. The asymmetrical embodiment 30 can be specifically contoured to conform to either the left ear, as seen in FIG. 2, or to the right ear (not shown). Left or right ear specific masks 30 are asymmetrical with respect to a vertical plane 35 bisecting the lower orifice 31 of the mask 30. The symmetrical embodiment mask 40 is shaped symmetrically about its vertical plane 45. The symmetrical mask 40 has the advantage of being usable to treat either the left or the right ear but has the disadvantage of somewhat compromising the conformance of the plug to either ear, sacrificing some heat transfer efficiency but still being acceptable for the purposes herein disclosed.

The leading contour of the envelope 10 or 20 has been contoured to approximate the trailing surface of its mask 30 or 40 when the tip 11 or 21 of the envelope 10 or 20 has been inserted through the orifice 31 or 41 of its mask 30 or 40. The volume of the envelope 10 or 20 has been determined so as to contain a quantity of the selected phase change chemical as will maintain the desired temperature, approximately 104° F., for approximately for thirteen to fifteen minutes.

The trigger 50 or 60 is designed to include the disk 51 or 61 and, if necessary, the support structure 53 which conforms the perimeter of the trigger 50 or 60 to the perimeter of the mask 30 or 40.

The plastic components, being the cap 54 or 64 and the mask 30 or 40, may be formed by injection molding. The envelope 10 or 20 may be formed by the use of technology similar to the technology used in making condoms. The trigger 50 or 60 can be cut and formed from a thin sheet of steel. The liquid chemicals are obtained by melting the selected salt.

After the trigger 50 or 60 is introduced into the envelope 10 or 20 through the aperture 14 or 24 in the throat 13 or 23, the phase change chemicals are injected in their liquid state through the aperture 14 or 24 into the envelope 10 or 20. Residual air is removed from the envelope 10 or 20 and then the envelope 10 or 20 is hermetically sealed. The envelope 10 or 20 is then seated in its mask 30 or 40 by inserting the leading tip 11 or 21 of the envelope 10 or 20 through the orifice 31 or 41 of its mask 30 or 40 and the perimeter of the trigger 50 or 60 is engaged in the perimeter of its mask 30 or 40 with the perimeter of the envelope 10 or 20 clamped there between. The cap 51 or 61 is then inserted into the opening 52 or 62 of disk 51 or 61, engaging the throat 13 or 23 of the envelope 10 or 20 between the cap 54 or 64 and the perimeter of the opening 52 or 62. Thus the rear wall of the reservoir 12 or 22 is linked to approximately the apex of the disk 51 or 61 of the trigger 50 or 60.

By way of example, it is anticipated that the asymmetrical embodiment will be shaped for the left ear, the right ear plug being an opposite hand version of the left ear plug shown, and the symmetrical embodiment will serve either ear. The anticipated dimensions for a polyurethane envelope 10 or 20 containing a water solution of sodium acetate would be such that the maximum vertical height of the mask 30 or 40, reservoir 12 or 22 and trigger 50 or 60 would be 28 millimeters and the maximum width of the plug would be 15 millimeters. The diameter of the lower orifice 31 or 41 in the mask 30 or 40 would be approximately 13 millimeters and the diameter of the upper orifice 33 would be approximately 6 millimeters. If the tip 11 or 21 of the envelope 10 or 20 has walls thinner than the walls of the remainder of the envelope 10 or 20, then the maximum diameter of the thinner walled tip 11 or 21 is approximately 6 millimeters. The tip 11 or 21 of the envelope 10 or 20 extends forwardly of the base diameter of the mask orifice 31 or 41 by 10 millimeters. From the base of the lower orifice 31 or 41 to its rear perimeter, the mask 30 or 40 is approximately 7 millimeters deep. From the rear perimeter of the mask 30 or 40 to the rearward most part of the reservoir 12 or 22 overlying the disk 51 or 61, being approximately the depth of the disk 51 or 61, the distance is approximately 4 millimeters. These dimensions are approximate and are based on use by an average adult. Plugs intended for use by infants or children may differ significantly, based on the criteria for dimensions herein given.

Operation

In operation, holding the plug with two fingers, it is inserted into the appropriate ear until, as seen in FIG. 7, the tip 111 or 21 enters the ear canal and the leading surface of the mask 30 or 40 makes contact with the surface S of the outer ear surrounding the entry E to the ear canal C. Once the plug is comfortably seated in this position, as seen in FIG. 8, the index finger is used to push the apex of the disk 51 or 61 toward the ear canal C until a click is heard. The clicking transformation of the disk 51 or 61 from its convex to its concave condition relative to the mask 30 or 40 activates the plug, initiating phase change of the chemicals from liquid to solid state. The index finger continues to hold the disk 51 or 61 in its concave condition for approximately 30 seconds until, as seen in FIG. 8, with the tip 11 or 21 expanded deeper into and widened into greater conformance with the walls W of the ear canal C, the crystallized chemicals have solidified the envelope 10 or 20 in the mold provided by the contour of the ear canal C. Thus, the tip 11 or 21, which is now warm and solid, is adhered to the wall W of the ear canal C. The index finger can be removed after solidification and the plug left in place for the time that the plug maintains its approximately 104° F. temperature. When the warming effect diminishes, as may be detected by contact with the index finger or by the change in color of a thermo-chromatic envelope 10 or 20, the plug is gently removed from the ear and discarded. Looking at FIGS. 4–6, a string 67 or the like, can be attached to the cap 64 to facilitate removal of the plug from the ear.

Thus, it is apparent that there has been provided, in accordance with the invention, a disposable plug for warming the inner ear that fully satisfies the objects, aims and advantages set forth above. While the invention has been described in conjunction with specific embodiments thereof, it is evident that many alternatives, modifications and variations will be apparent to those skilled in the art and in light of the foregoing description. Accordingly, it is intended to embrace all such alternatives, modifications and variations as fall within the spirit of the appended claims.

What is claimed is:

1. For generating heat to warm an ear canal, a disposable plug comprising a mask for abutment against a portion of the outer ear surrounding the entrance to the ear canal, a sealed envelope having a leading elastic tip extending forwardly of said mask for insertion into the ear canal and a trailing reservoir extending rearwardly of said mask, a super-cooled liquid salt at approximately room temperature substantially filling said envelope and manually operable means disposed in said envelope reservoir for reducing a volume of said reservoir to expand said tip into deeper extension into said ear canal and for activating solidification of said liquid salt to generate heat.

2. A disposable plug according to claim 1, said mask being rigid.

3. A disposable plug according to claim 1, said envelope being made of polyurethane.

4. A disposable plug according to claim 1, said liquid salt being a water solution of sodium acetate at approximately room temperature.

5. A disposable plug according to claim 1, said tip of said envelope being symmetrical in relation to a vertical plane.

6. A disposable plug according to claim 1, said mask and said tip of said envelope being symmetrical in relation to a vertical plane.

7. A disposable plug according to claim 1, said envelope having walls of constant thickness.

8. A disposable plug according to claim 1, walls of said envelope tip being thinner than walls of said envelope reservoir.

9. A disposable plug according to claim 1, said envelope being hermetically sealed.

10. A disposable plug according to claim 1, said envelope having thermochromatic pigmentation.

11. A disposable plug according to claim 1, said envelope containing a sufficient quantity of said super-cooled liquid salt to maintain a temperature of approximately 104° F. for at least approximately 13 to 15 minutes after activation thereof.

12. For generating heat to warm an ear canal, a disposable plug comprising a mask insertable into abutment against a portion of the outer ear with an orifice at an entry to the ear canal, a sealed envelope disposed through said orifice with a leading elastic tip extending forwardly of said orifice for insertion into the ear canal and a trailing reservoir extending rearwardly of said orifice and abutting said mask, a super-cooled liquid salt at approximately room temperature substantially filling said envelope and manually operable means disposed in said envelope reservoir for reducing a volume of said reservoir to expand said tip into deeper extension into said ear canal and for activating solidification of said liquid salt to generate heat.

13. A disposable plug according to claim 12, said manually operable means comprising a convex disk disposed in said envelope reservoir and immersed in said liquid salt, means connecting said reservoir to approximately an apex of said disk and means clamping a periphery of said mask against a periphery of said disk with a periphery of said reservoir therebetween, whereby pressing said disk with said tip inserted into the ear canal and said mask abutting the outer ear causes said disk to pop from convex to concave, reducing a volume of said reservoir to expand said tip into deeper extension into and compliance with said ear canal and activating solidification of said liquid salt to generate heat.

14. A disposable plug according to claim 12, said convex disk being metallic.

15. A disposable plug according to claim 12, said convex disk having an opening at an apex thereof.

16. A disposable plug according to claim 15 further comprising a cap insertable into said disk opening with a portion of a rear wall of said reservoir therebetween to fix said wall portion to said disk apex.

17. A disposable plug according to claim 12, said mask having a second orifice.

18. A disposable plug according to claim 17, said second orifice being above said orifice at the entry to the ear canal.

19. A disposable plug according to claim 12, said mask having at least one groove extending rearwardly from a perimeter of said orifice.

20. For generating heat to warm an ear canal, a disposable plug comprising a mask having a wall with an orifice therethrough, said wall being contoured for insertion into abutment with an outer portion of the ear with said orifice aligned with and at an entry to the ear canal, a sealed envelope having a leading tip extending forward of said orifice and a trailing reservoir extending rearward of said wall of said mask, said tip being contoured for insertion into the ear canal and being elastic and said envelope reservoir having a forward wall, a main body and a rear wall, said forward wall being contoured for compliance against said wall of said mask, a super-cooled liquid salt substantially filling said envelope, a convex disk disposed in said reservoir and immersed in said liquid salt, means connecting said rear wall of said reservoir to said disk and means clamping a periphery of said mask against a periphery of said disk with a periphery of said body of said envelope therebetween, whereby popping said disk from convex to concave with said tip inserted into the ear canal expands said tip into deeper extension into and compliance with said ear canal and activates solidification of said liquid salt to generate heat into the ear canal.

* * * * *